United States Patent [19]

Shah et al.

[11] 4,303,530
[45] Dec. 1, 1981

[54] BLOOD FILTER

[75] Inventors: Suresh T. Shah, Edina; Miles C. Huffstutler, Jr.; Bruce D. Bentzen, both of Burnsville, all of Minn.

[73] Assignee: Medical Incorporated, Inver Grove Heights, Minn.

[21] Appl. No.: 845,649

[22] Filed: Oct. 26, 1977

[51] Int. Cl.³ .............................................. B01D 13/00
[52] U.S. Cl. ..................................... 210/651; 210/489
[58] Field of Search ............... 210/DIG. 23, 489, 493, 210/23 R, 651

[56] References Cited

U.S. PATENT DOCUMENTS

| | | | |
|---|---|---|---|
| D. 238,456 | 1/1976 | Mouwen | D83/12 A |
| 2,736,436 | 2/1956 | Fresch | 210/494 X |
| 3,026,609 | 3/1962 | Bryan | 210/494 X |
| 3,262,578 | 7/1966 | Dennis | 210/489 |
| 3,276,597 | 10/1966 | Mesek et al. | 210/489 |
| 3,593,884 | 7/1971 | Swank | 210/436 |
| 3,701,433 | 10/1972 | Krakauer | 210/DIG. 23 X |
| 3,765,536 | 10/1973 | Rosenberg | 210/DIG. 23 X |
| 3,827,562 | 8/1974 | Esmond | 210/304 |
| 3,935,111 | 1/1976 | Bentley | 210/DIG. 23 X |
| 3,972,818 | 8/1976 | Bokros | 210/435 |

Primary Examiner—Frank A. Spear, Jr.
Attorney, Agent, or Firm—Bruce A. Jagger

[57] ABSTRACT

A blood filter in which the pore size of the filtering media generally decreases through a series of at least three stages where the filtering capacity of at least the first stage is chosen so as to accommodate without substantial impairment of function the quantity of large particle size debris which is normally present in a predetermined amount of blood. The filtering media is composed of several plies of porous material including both depth and screen filter elements. These filter elements are arranged in one or more elongated bands. The bands are spirally wound into a cylindrical form around a generally rigid, perforate core. The ends of the spirally wound cylindrically configured filter are sealed to produce a filter cartridge. The filter cartridge is in turn sealed into a container which has blood inlet and outlet ports arranged so that blood normally flows radially inwardly through the filter.

17 Claims, 17 Drawing Figures

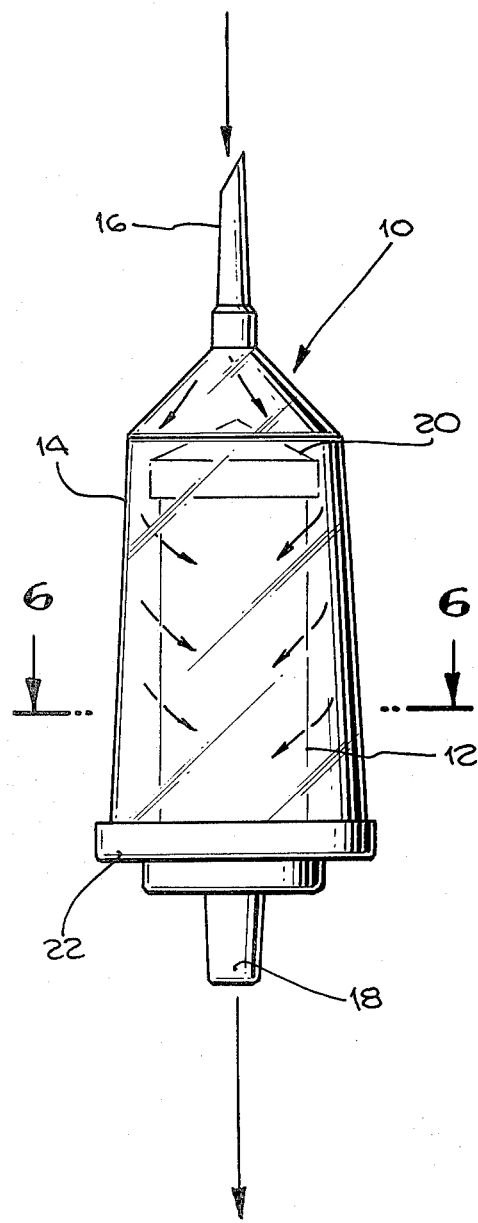
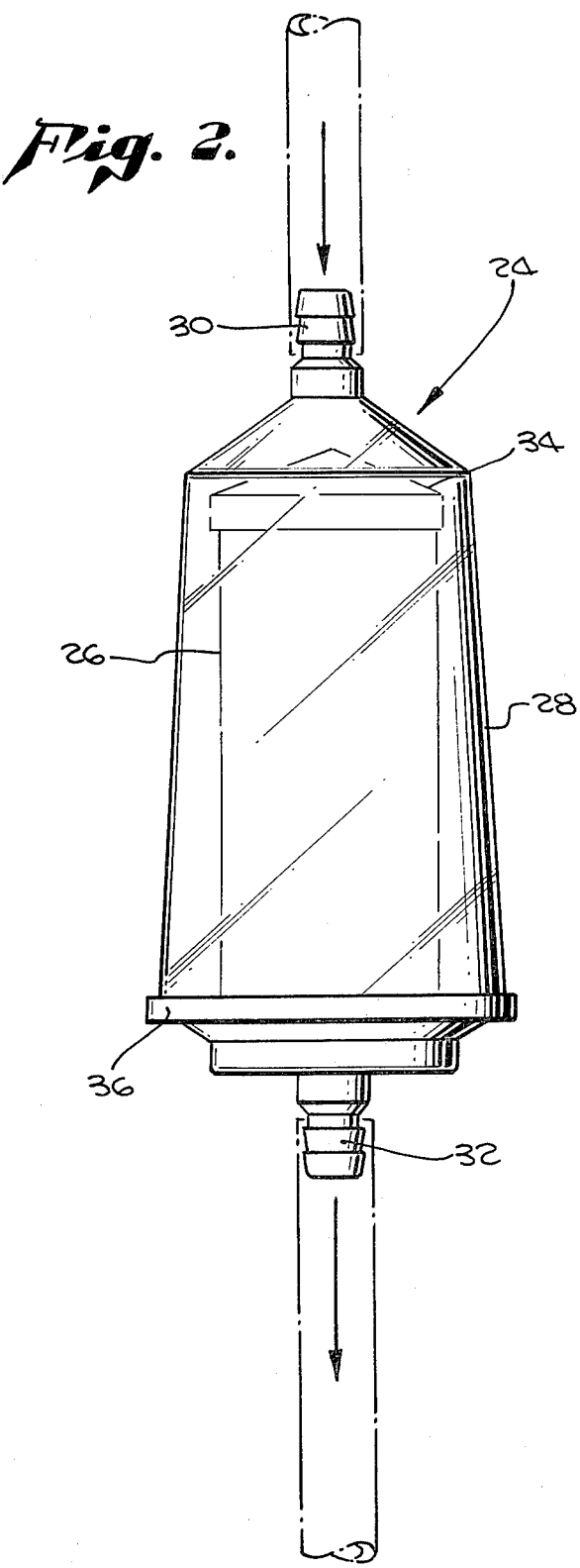

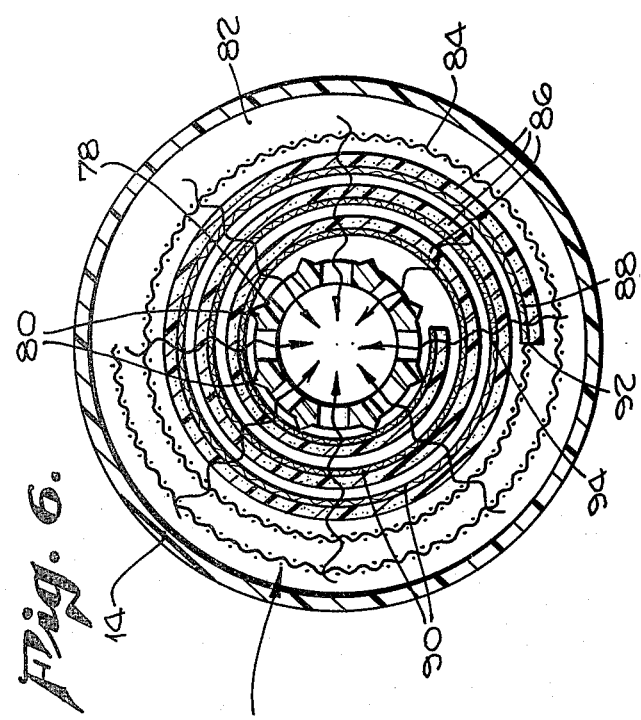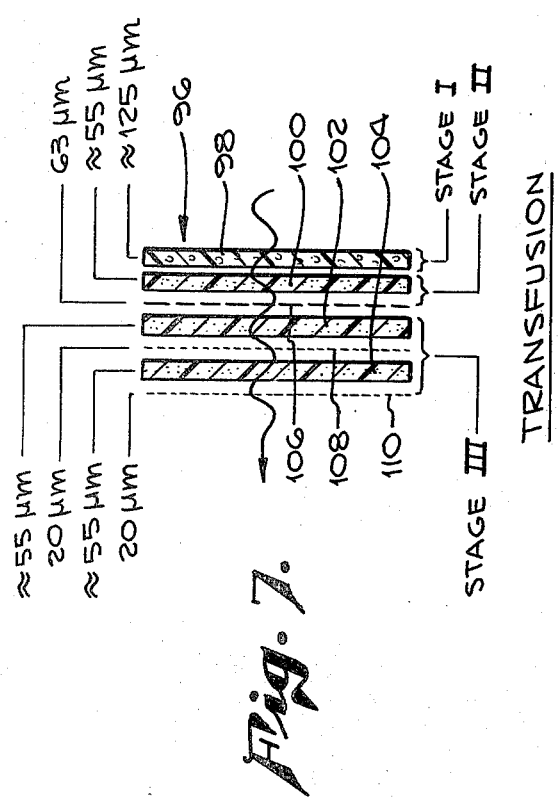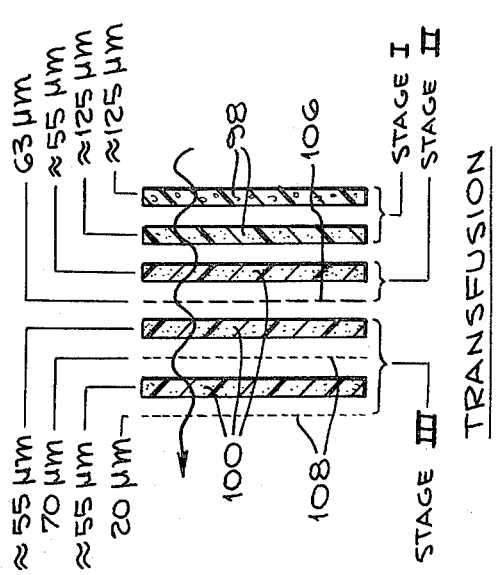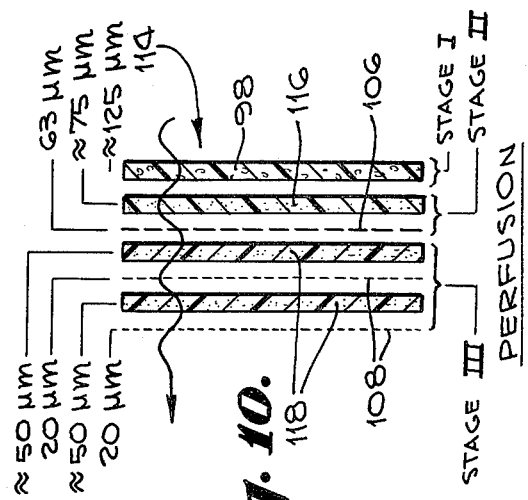

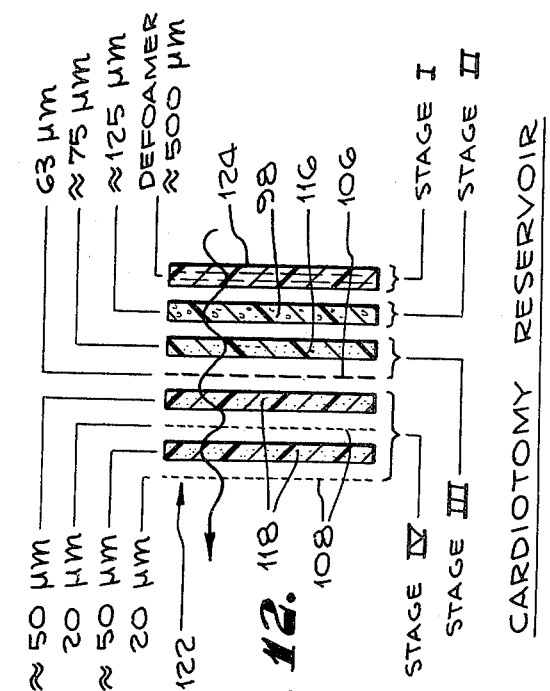

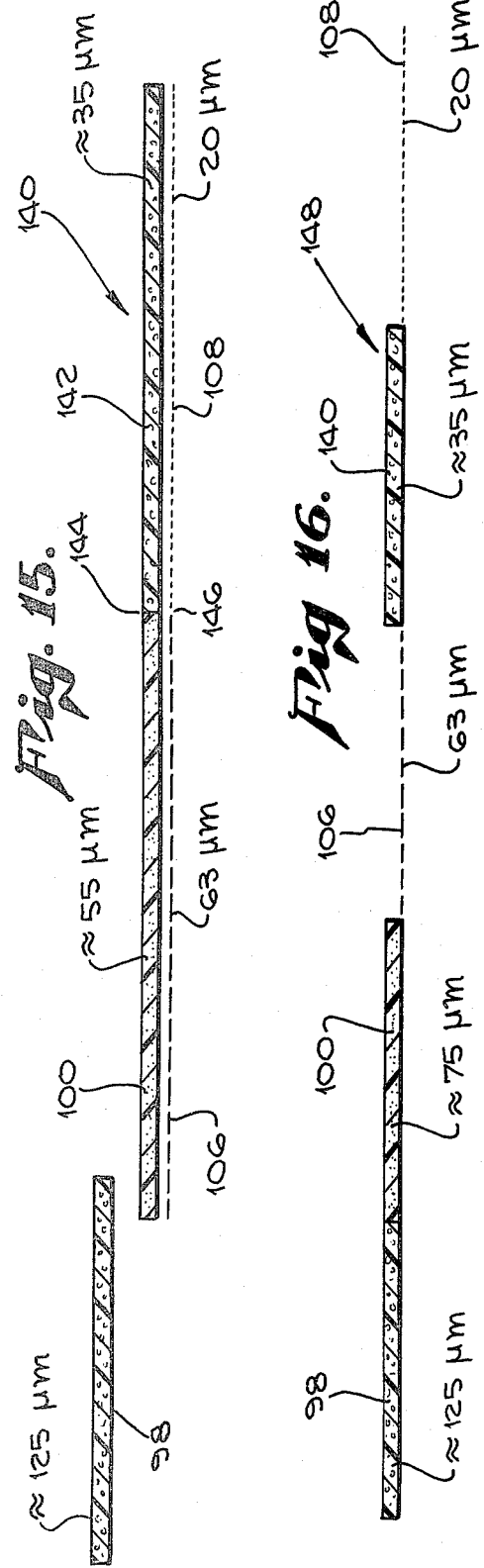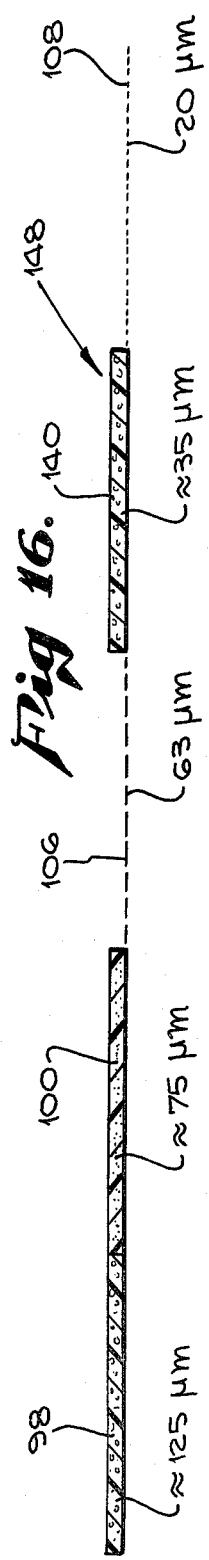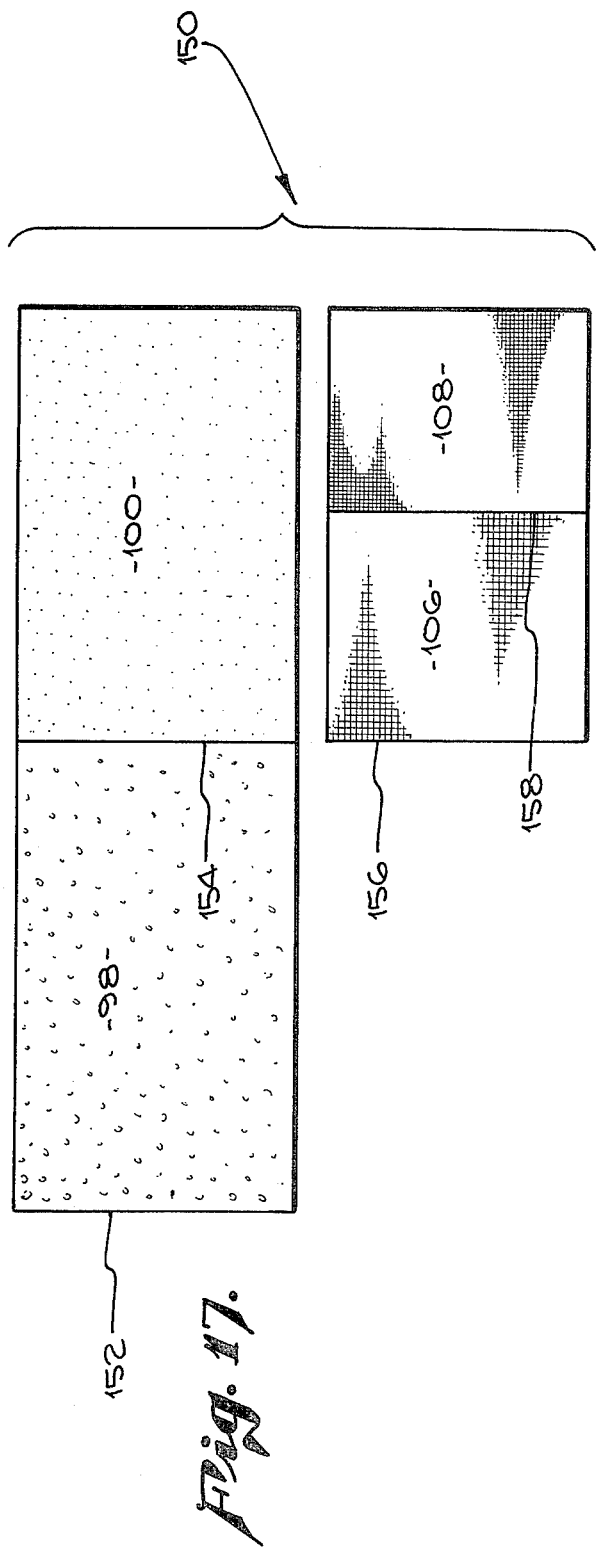

BLOOD FILTER

Previously, considerable difficulty had been experienced in filtering blood so as to remove gas and solid microemboli therefrom. Previous filters tend to exhibit substantially decreased flow rates, large pressure drops, and substantial reductions in the effectiveness of the filtration action after the passage of a relatively small amount of blood therethrough. These and other disadvantages of the prior art have been overcome according to the present invention wherein an effective, high capacity, low prime volume, high flow rate blood filter is provided. Filtration is accomplished, according to the present invention in a plurality of filtration stages. Blood which these filters are intended to purify generally includes microemboli which range in size from as much as 300 or 400 microns down to approximately 20 microns. The individual red and white cells are generally smaller than 20 microns. The particle sizes of the blood debris are distributed throughout a plurality of size fractions. A filtration stage can be provided for each selected size fraction with the coarsest size fraction generally containing all particles with a principal dimension in excess of approximately 100 microns. At least two other stages are provided in the filter to remove and retain size fractions wherein the particles have a size of less than 90 microns. The size distribution of the blood debris differs depending upon the history of the blood. Blood which has been in storage in a blood bank, for example, usually has more large size particles than blood passing through an extracorporeal system such as an oxygenator or dialyzer.

The filtering elements which are incorporated in blood filter devices according to the present invention incorporate both depth filter elements and screen filter elements. Screen filter elements generally have a substantially uniform pore size and retain their original pore size during use. Screen filter elements are substantially two dimensional in nature. Depth filter elements are three dimensional in nature. The pore diameters in depth filter elements are typically not uniform in size. Depth filter elements generally have large filtering capacities as compared with screen filter elements in that depth filter elements can retain large amounts of debris as compared to screen filter elements. Screen filter elements, because of their uniform pore size, tend to produce a much cleaner cut in particle sizes between the "retained" and the "pass" size fractions. In order to realize the benefits of the present invention, the filter elements are arranged in series so that the blood contacts a depth filter first in each filtration stage. Where it is desired to ensure that substantially no large particles pass into the subsequent stage, a screen filter element is employed. In general, the screen filter element is selected so as to have a pore size which is several microns smaller than the average pore size of the depth filter which precedes it. Additional performance stages may be added, if desired, to ensure thorough removal of a selected size fraction.

Because the debris to be removed is generally gelatinous, blood is difficult to filter. Under pressure the blood debris exhibits a soft plastic nature and may be extruded through a screen filter element, or it may break up into smaller particles. Inherent in the nature of certain depth filtering elements is a tendency to form channels which may exaggerate the extrusion or break up of debris or become sufficiently enlarged to permit large particle sized debris to pass through them. Channelization is particularly a problem when the filter elements in one or more stages become partially blocked and high pressure gradients develop. The risk of a large debris particle slipping through a filtration stage because of channelization is minimized by placing a screen filtering element immediately adjacent to the downstream side of a depth filtering element. Even when screen filtering elements are used in series with depth filtering elements, high pressure gradients are undesirable because elevated pressure also tends to cause damage to the blood itself and may even cause hemolysis.

The filtering capacity of the various filtration stages, according to the present invention, is such that a large quantity of blood can be passed through the filter without creating a large pressure drop across the filter or any of its stages and without restricting the flow to the point where it is not adequate for its intended purposes. The various filtration stages are designed, insofar as possible, so that each stage will accommodate the flow of about the same amount of blood before it becomes overloaded to the point where reduced flows or excessive pressure drops dictate its discard. Ideally, each of the filtration stages should reach its overload point at about the same time. In practice, the structural configuration of the filter generally dictates that one or more of the stages will have some degree of excessive capacity relative to the others. Safety considerations may also dictate that at least the last stage may have a large excessive capacity relative to the other stages.

According to one preferred embodiment, the filtering cartridge is formed by preparing a long band which is composed of a plurality of filtering element segments. The band contains both depth and screen filter element segments which are joined to one another at their abutting edges so as to form a continuous band. The band is spirally wound in a cylindrical form on a rigid perforate core element so that the pore sizes generally decrease from the outside to the inside of the resultant cylindrical filtering cartridge. Two or more bands may be wrapped together if desired. The ends of the resultant filter are sealed so as to force the blood to flow along radial paths from the exterior of the cylindrical cartridge to the rigid perforate core through a concentrically arranged filter elements. The arrangement of the segments in the band dictates where along the radial flow paths the various pore sizes will occur. For certain embodiments, a segment may be of such a length that it extends along its spiral path for more than 360 degrees around the cartridge. This results in the blood contacting this particular element more than once. Thus, there may be filtering elements which have larger pore sizes than some one or more filtering elements which are upstream from them along the normal radial flow path of the blood. In general, however, the pore sizes decrease as the blood flows downstream along its normal flow path through the filter cartridge.

Preferably, the pore size of the outermost filtering element is sufficient to trap and hold blood debris which has a principal dimension in excess of approximately 100 microns. The filtration characteristics of the outermost filter element are generally selected so that the smallest particles retained are generally larger than approximately 90 microns and often are approximately 125 microns in their principal dimension. The outermost filtering element is a depth filter, which is capable of retaining debris which has particle sizes in excess of from approximately 90 to 150 microns. The smallest pore size used in the last filtration stage is generally approximately 20 microns. Pore sizes substantially smaller than 20 microns tend to filter out some individual red and white cells; this is highly undesirable in applications where these devices are generally employed.

In order to provide effective filtration and adequate debris retention capacity at each stage of filtration, it has been found that at least three stages are required. More than one type of filtering element may be used in each stage. In general, both depth and screen filtering elements are used at least in those stages which occur between the first and the last stages. The first stage may only include a depth filter and the last stage may only have a screen filter. In general, the particle sizes of the smallest particles retained on the first filtering stage depth filter range from approximately 90 to 150 microns; those retained in the second stage range from approximately 40 to 80 microns; and those retained in the third stage are approximately 20 microns. Additional stages may be used if desired, and filter elements from one stage may be placed in adjacent stages so long as the pore sizes generally decrease from the inflow to the outflow side of the filter cartridge. Increased capacity or safety may be achieved, if desired, by using filter elements from one stage in adjacent stages.

One reason for using a blood filter is that microemboli, when permitted to enter the blood stream of a living human being, create the serious possibility that the function of certain vital organs, such as the brain and the kidneys, may be compromised or that a blood flow channel or capillary may be blocked. The microemboli may take the form of gas bubbles or aggregated particulate material. When human blood is stored for use in transfusions, its leukocyte and platelet components are altered. Some of the platelets agglomerate and form clumps of varying sizes. Also, some of the platelets form aggregates with some of the leukocytes. In addition to use in transfusions, blood filters, according to the present invention, are useful in arterial/perfusion, cardiotomy reservoirs, cardiotomy, and dialysis. The filters provide very consistent filtration operation under conditions of high flow for use in extracorporeal circulation circuits.

The blood filter cartridge can be constructed with one, or a plurality of bands, each of which is composed of a plurality of segments with the segments being joined end to end with butt joints or overlapped with or without being joined. The characteristics of a single segment of a band may vary along its length; for example, when knitted bands are used, the knitting may be varied to some extend along the length of the segments so that progressively smaller pore openings are produced in that segment. The various segments may consist of depth filter elements, such as foams, fibers, felts, and knit fabrics, singularly or in combinations, and screen filter elements such as woven or extruded meshes and perforated webs. The segments must be constructed of material which is compatible with blood. Generally, the length of each segment in the series ranges from 1.05 to 3.15 times the nominal circumference of the filter cartridge at the location where the segment occurs in the spirally wound cartridge. The length of each segment is generally sufficient to ensure a slight overlap. In order to provide the desired predetermined pore volume in each wound layer of the completed filter cartridge, the filter elements are selected according to both pore size and volume fraction porosity. The requirement that there be a sufficient pore volume to provide the desired capacity at each stage of filtration may dictate that a particular band segment be long enough to make more than one wrap.

The approximate tailoring of the filtering capacities of the various filtration stages so as to approximately match the quantity of debris which occurs in a given predetermined volume of blood permits the size of the blood filter to be reduced so that it requires only a small volume of blood to prime it. Blood filter devices, according to the present invention, which exhibit high filtration capacities, high flow rates, low priming volume, and continuous operation with the functions of contemporaneously filtering and deaerating the blood are uniquely and unexpectedly superior.

The filter cartridge in its preferred spirally wound cylindrical form may be supported on its exterior by a material with relatively coarse openings. This exterior supporting member has openings which are generally too large to function as filtering elements.

In a preferred embodiment a knitted mesh material is used as the outermost filtering element. Knitted material exhibits some of the characteristics of both depth and screen filters. Knitted mesh filters have a large retention capacity as compared with screen filter elements. The pore sizes in a knit mesh filter element are generally not uniform, but the pore sizes tend to retain their as manufactured sizes during use. When two or more wraps of knitted mesh material are placed on the outside of the filter so that the blood sees several plies of knit mesh material as it passes radially inwardly towards the rigid perforate core a particularly effective result is achieved. The two or more layers of knit mesh function so as to provide a very large retentive capacity for blood debris while also producing a relatively clean cut in the particle sizes. It is therefore generally not necessary to use a screen element in the first stage. This reduces the weight complexity, size, and expense of the filter as well as simplifying its construction. The knit mesh has been found to be a good structural material so that the structural integrity of the filter cartridge is assured by the use of at least a double layer of this knit mesh material as the outermost stage in the filter. Single plies of knit mesh are also effective for the intended purposes.

The knit structures that exhibit the characteristics of both depth and screen elements may be manufactured, for example, utilizing flat warp knitting and other knitting procedures. The yarn may be in the form of either monofilament or multifilament. In general, if a multifilament yarn is used, it should have a slight S or Z twist. The fiber should be a blood compatible polymeric material, such as, for example, polyester, polyethylene, polypropylene, polyamide, polyimide, polytetrafluoroethylene, or the like. In general, the multifilament yarn has has a denier (grams per 9,000 meter length of yarn) of from about 20 to 400 and different denier yarn may be incorporated in the same knit structure. The structure of the yarn is such that it may have from about 20 to 100 courses per inch and from about 10 to 50 wales per inch.

The knitted fabric is manufactured so that it has an inherent tendency to curl into a cylinder which tends to urge it into a spirally wound configuration. This aids the manufacturing process by tending to force the filter elements to assume the desired spirally wrapped configuration. The tendency to curl also assists in maintaining the spirally wrapped configuration once it has been manufactured. The tendency to curl around the longitudinal axis of the filter contributes to the production of a smooth and even filter cartridge.

The knit structure at the exterior of the filter contributes significantly to the gentle and efficient way in which the filter handles blood. Transfusion filters are often used with very low blood flow rates of, for example, 10 to 20 milliliters per minute. At these flow rates the blood is entering the filter in a dropwise fashion. The drops of blood, according to the present invention, enter the main body of the filter by flowing into contact with a conical surface under the urging of gravity. The spacing of the conical surface from the inflow side of the filter is small so that the blood does not drop on the conical surface with any significant force. The blood flows downwardly over the conical surface and over the edge thereof into contact with the knit structure at the exterior of the filter cartridge. The nature of the knit structure is such that the drops of blood tend to spread out to form a sheet as the blood moves downwardly through the knit structure along the exterior of the filter until it reaches the liquid level in the filter. The sheet of blood merges gently with the liquid at the liquid level without causing any splashing or trauma. If a drop of blood is permitted to form at the top of the filter so that it drops into the liquid, a splash will result and some blood may contact the interior wall of the filter case or shell above the liquid level. This splashed blood will tend to dry and clot which results in the loss of some of the blood as well as increasing the amount of blood debris which must be filtered. The falling of a drop of blood through a distance of several centimeters also may cause the blood to be damaged when it impacts the liquid surface.

In general, knit structures prepared from monofilaments are preferred for use according to the present invention. It has been found that knit structures produced using multifilament yarns do not give results that are as satisfactory as those achieved using knit structures made from monofilaments. In general, monofilaments having thicknesses of from about 2 to 30 mils, and preferably from about 4 to 8 mils, may be used in preparing knit structures according to the present invention. If multifilament yarns are to be used, they are generally more satisfactory in extracorporeal circuits where large blood clots are generally not encountered. Care should be taken to avoid abrading the yarn so that individual fibers do not break off and enter the blood.

The nature of the knit structure is such that there are several different pore sizes which have different characteristics within the structure. These pore sizes repeat with considerable uniformity as the stitch pattern repeats itself.

The exposed edges of the knit structure are fused so that loose pieces of filament and sharp filament ends are not present in the structure.

The joining of the various filter elements into a continuous band facilitates the manufacturing of the filter and assures that the filter elements will be positioned in the filter at the desired locations without any gaps or excessive overlaps which might impair the efficiency of the filter. If it is desired to use a filter element which is not to be joined end to end with the other filter elements in a continuous band, care should be taken to ensure that it is positioned in the proper desired location. Several bands may be wrapped together if desired; for example, all of the depth filter elements may be joined in one band while all of the screen filter elements are joined end to end in a second band.

The core should be rigid enough to support the filter structurally and open enough to permit the blood to flow freely through the core. The core should be shaped as much as possible so as to avoid forcing the blood to flow through small areas in the innermost filter elements. In order to accomplish this the contact between the filter and the core should be in the form of line or point contact rather than area contact, insofar as is possible.

The stitch pattern of the knit structure is preferable, one which has a closed stitch on the front bar and a lay in stitch on the back bar. The closed stitch tends to cause the structure to curl towards the closed side and the lay in stitch orient the curling tendency around the longitudinal axis of the filter as well as promoting the sheet like flow of the blood. The stitch pattern on the front bar is conveniently a 1-0, 2-3; or 1-0, 1-2; or 1-0, 3-4; or the like closed pattern, while that on the back bar is conveniently a 0-0, 4-4; or 0-0, 1-1; 0-0, 8-8; or the like lay in pattern. Any desired gauge may be used depending upon the desired particle size fraction and the diameter of the monofilament or yarn. In general, gauges (needles per inch) of from about 10 to 30 are useful with the higher gauges being used with smaller diameter monofilaments.

The segments of the bands which are wound into the spiral filter structure may be joined by any convenient method, such as, for example, thermal welding, sewing, adhesive joining, radio frequency welding, laser welding, ultrasonic welding and the like. The joints may be in the form of lap joints, butt joints or the like. The band may be constructed so that all or a part of the unwrapped band includes more than one ply. For example, one segment of the band may include two plies of screen which are coextensive with one another and both of which are joined to adjacent segments. The use of plural plies at one or more locations in the band with all of the plies being joined to the band by at least one end avoids the use of loose filter elements in the structure while providing an additional filter element where desired in a particular stage. The avoidance of loose segments is an advantage in manufacturing.

Where separate bands are laid loosely over one another without being bonded, they are generally conveniently handled during manufacturing as a single unit.

The ends of the filter cartridge are sealed by potting them with a blood compatible resin which is cured in situ. One end of the cartridge is capped with a cap which has a generally shallow conical form. The other end of the cartridge is potted into a receptacle so that it is held in position within the filter case, and in sealed relationship with the exhaust side of the filter. The shallow conical gap causes blood to distribute itself around the circumference of the filter. Blood flowing into the filter falls approximately on the point of the conical cap so that it flows outwardly in all directions over the surface of the conical cap. The filter cartridge is confined within a shell which provides both inlet and outlet connections. The shell is generally annular in shape with the filter cartridge being centrally located therein. There is an annulus defined between the inner wall of the shell and the outer side of the filter cartridge. This annulus serves as a manifold to direct blood flow to the entire outer circumference to the filter cartridge.

The filter can, if desired, incorporate a drug delivery system in that the structure of the filter may be doped with, for example, anticoagulants, vitamins, hormones, antibiotics, antiseptics, and the like. The drugs may be incorporated in forms which have limited solubility so that the drug is released at a predetermined rate over a period of time.

Referring particularly to the drawings for the purpose of illustration and not limitation, there is illustrated:

FIG. 1 is an elevational view of a blood transfusion filter according to the present invention;

FIG. 2 is an elevational view of a cardiotomy filter according to the present invention;

FIG. 6 is a cross sectional view of a transfusion filter taken along line 6—6 in FIG. 1;

FIG. 7 is an exploded cross-sectional view taken along a plane including a radial flow path through a transfusion filter according to the present invention;

FIG. 8 is an exploded cross-sectional view of a further embodiment taken along a plane including a radial flow path through a transfusion filter according to the present invention;

FIG. 9 is an exploded cross-sectional view of an additional embodiment taken along a plane including a radial flow path through a transfusion filter according to the present invention;

FIG. 10 is an exploded cross-sectional view taken along a plane including a radial flow path through a perfusion filter according to the present invention;

FIG. 11 is an exploded cross-sectional view taken along a plane including a radial flow path through a cardiotomy filter according to the present invention;

FIG. 12 is an exploded cross-sectional view taken along a plane including a radial flow path through a cardiotomy reservoir according to the present invention;

FIG. 13 is an edge view of filter elements prior to being wrapped around a rigid core;

FIG. 14 is an edge view of a further embodiment of a plurality of filter elements prior to their being spirally wound around a core;

FIG. 15 is an edge view of a further embodiment of a plurality of bands prior to their being spirally wound around a core;

FIG. 16 is an edge view of a additional embodiment of an integral band; and

FIG. 17 is a plan view of the filter elements of an embodiment of the present invention prior to their being assembled into a spirally wound filter.

Figure 3:
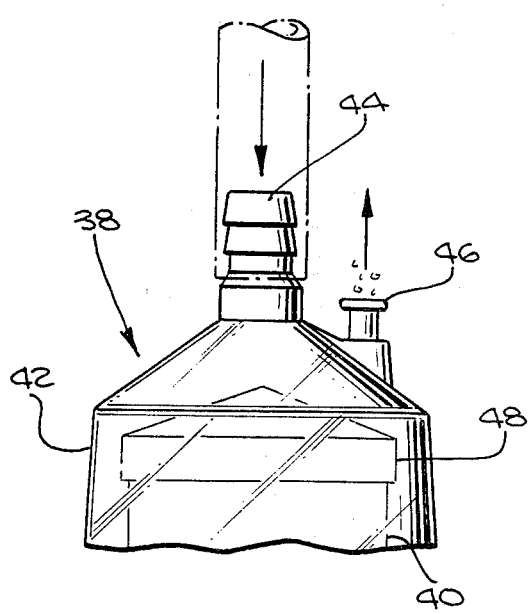
FIG. 3 is a partial elevational view of a perfusion filter according to the present invention.

Referring particularly to the drawings, there is illustrated generally at 10 a transfusion filter in which a filter cartridge 12 is positioned within a transparent shell 14; an inlet 16 is provided at the normally upper end of shell 14; and an outlet 18 is provided at the normally lower end of shell 14. Inlet 16 is provided with a point for insertion into a bag containing blood. A conical distributor cap 20 is positioned over and seals with the normally upper end of filter cartridge 12. The normally lower end of filter cartridge 12 is received in and seals with cap 22. The transfusion filter indicated generally at 10 is normally inserted into the bottom of a bag of blood and the filter receives the blood from the bag under the urging of gravity.

Referring particularly to FIG. 2, there is indicated generally at 24 a cardiotomy filter. The cardiotomy filter has generally the same configuration as the transfusion filter; however, it is intended to be used between a cardiotomy reservoir and an oxygenator in open heart surgery where the extracorporeal circulation may be as high as 6 to 8 or even 10 liters per minute. The pressures and flow rates through cardiotomy filter 24 are much higher than the pressures and flow rates through transfusion filter 10 under normal operating conditions. Cardiotomy filter 24 includes a generally cylindrically spirally wound filter cartridge 26 which is positioned within shell 28. Shell 28 is provided with an inlet 30 at the normally upper end of the filter 24 and an outlet 32 at the normally lower end of cardiotomy filter 24. The blood flows downwardly through inlet 30 and onto conical distribution cap 34 which spreads it uniformly around the annulus between the outer periphery of cylindrical filter cartridge 26 and the annular interior wall of shell 28. One end of filter cartridge 26 is sealed to conical distribution cap 34 and the other end is sealed in shell cap 36 so that blood is forced to flow radially inwardly from the outer periphery of filter cartridge 26 toward the core of the filter.

Referring particularly to FIG. 3, there is illustrated generally at 38 a perfusion filter which is intended to be used in an extracorporeal circuit during open heart surgery between the oxygenator and the inlet to the patient. This is a high pressure, high flow rate device. Perfusion filter 38 has a configuration which is very similar to that of cardiotomy filter 24 and includes a filter cartridge 40 which is postioned within a shell 42. Shell 42 is provided with an inlet 44 and an air vent 46. Conical distribution cap 48 performs the function of uniformly distributing blood around the annulus between shell 42 and filter cartridge 40.

Figure 4:
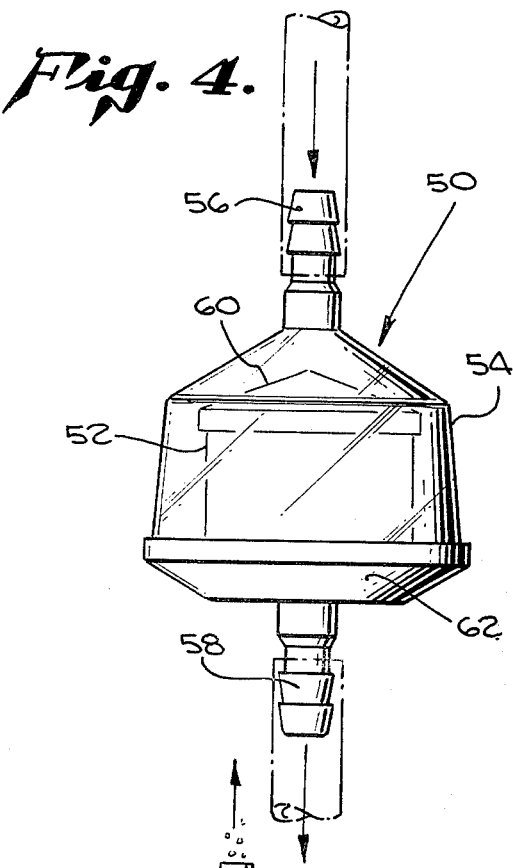
FIG. 4 is a blood filter according to the present invention for use with a kidney dialysis machine.

Referring particularly to FIG. 4, there is illustrated generally at 50 a dialysis filter. Dialysis filter 50 is intended for use with a blood dialysis machine. Dialysis filter 50 includes a filter cartridge 52, a shell 54 which is provided with an inlet 56, an outlet 58, and a shell cap 62. A conical distribution cap 60 is sealed to the normally upper end of filter cartridge 52. These elements are interrelated in generally the same way as previously discussed with reference to FIGS. 1, 2, and 3.

Figure 5:
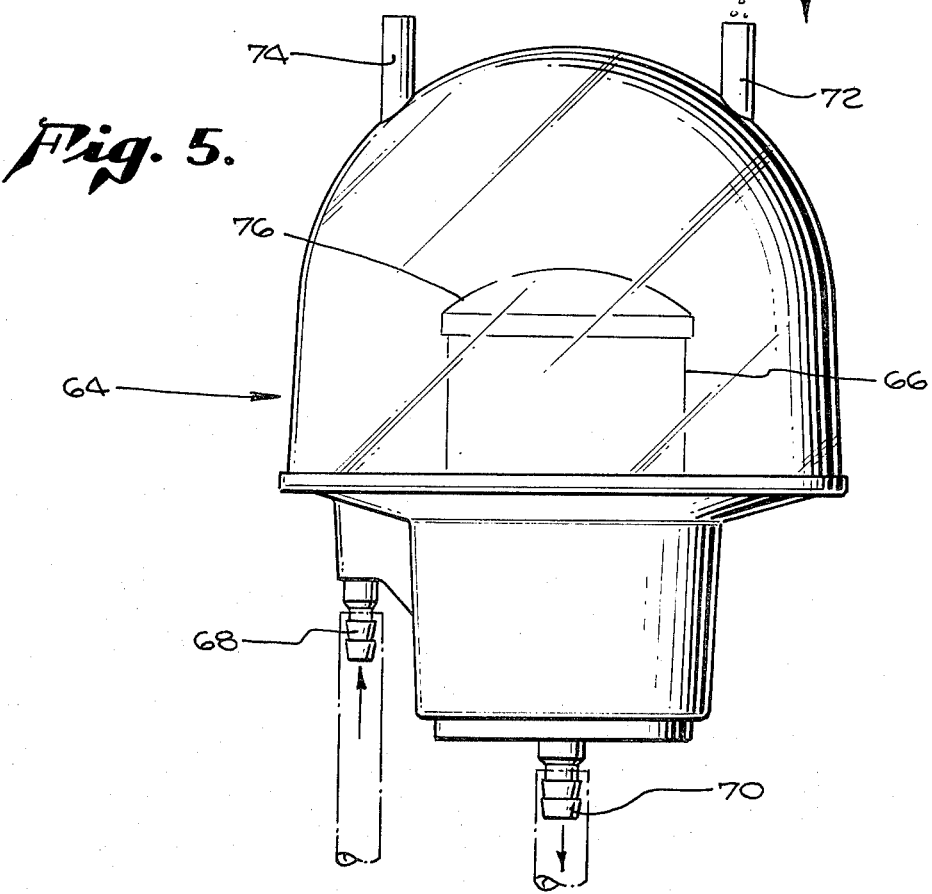
FIG. 5 is a cardiotomy reservoir blood filter according to the present invention.

Referring particularly to FIG. 5, there is indicated generally at 64 a cardiotomy reservoir. A cardiotomy reservoir is provided in an extracorporeal blood circulation circuit between the outlet from the patient and the cardiotomy filter upstream from the oxygenator. The cardiotomy reservoir 64 includes a filter cartridge 66 which is positioned so that blood flowing from blood inlet 68 through the cardiotomy reservoir to blood outlet 70 must pass through the elements of the filter cartridge 66. The blood leaves the reservoir as soon as it is filtered. The blood is stored here before it is filtered. An air vent 72 permits entrained air to be removed from the blood. The filter cartridge 66 preferably may include a defoamer stage. A medication inlet 74 is provided to permit the addition of desired drugs including for example, anticoagulant. A filter cartridge cap 76 is provided to seal one end of the cylindrically configured filter cartridge 66. The other end of filter cartridge 66 is sealed into a recess in the cardiotomy reservoir 64.

Referring particularly to FIG. 6, there is illustrated a cross-sectional view taken along line 6—6 in FIG. 1. The spiral wraps of the filter cartridge 12 are shown slightly separated from one another for clarity of illustration. As will be understood by those skilled in the art, the plies of filter cartridge 12 are in contact with one another in the filter. A perforate core 78 provides a rigid axial support for the filter cartridge. The projections 80 on perforate core 78 run axially of the core and serve to support the inner ply of the filter cartridge 12 so as to permit blood to flow readily into the ports in perforate core 78. In general at least 50 percent, and preferably at least 70 percent, of perforate core is open area. The annulus 82 fills with blood and surrounds the filter cartridge 12 so that blood flows as indicated radially inwardly through the filter and into the hollow axis of perforate core 78. The first filter element which is contacted by the blood as it moves from annulus 82 toward perforate core 78 is a polypropylene knit structure indicated at 84. The polypropylene knit structure, according to one preferred embodiment, filters out blood debris which has particle sizes in excess of approximately 125 microns. The second filter element 86 in the radially inward flow path of the blood is a polyurethane felt which retains blood debris having particle sizes in excess of approximately 55 microns. A polyester screen filter element 88 having a pore size of about 63 microns occurs next in the radial flow path. After passing through filter 88 the blood encounters another ply of filter element 86. After the second ply of filter element 86, the blood encounters a polyester screen filter element 90 in which the filter element has a pore size of about 20 microns. The blood finally encounters a third ply of filter element 86 and a second ply of filter element 90 before entering perforate core 78. The abutting ends of filter element 84, 86, and 88 are joined together at 92 so as to form a composite band structure. The abutting edges of filter elements 88 and 90 are joined together at 94 so as to form a single band which is wound around perforate core 78 in a spiral wrap.

Referring particularly to FIG. 7, there is illustrated an exploded cross section taken along the radial flow path in a transfusion filter cartridge indicated generally at 96. The path of the blood flow is as indicated. The depth filter elements are indicated at 98, 100, 102, and 104, respectively, and the screen filter elements are indicated at 106, 108, and 110, respectively. The smallest particles in the particle size fractions removed in the various stages are as indicated by the microns sizes shown in FIG. 7. The depth filter element which appears as element 100 reoccurs twice more in the radial flow path as elements 102 and 104. This depth filter element is a polyurethane felt having an uncompressed thickness of about one-sixteenth of an inch and a weight of approximately 8.47 ounces per square yard of felt. This felt has a pore count of approximately one hundered pores per linear inch. The felt has a specific area of approximately 900 square feet per square foot of felt. The polyester screen element 106 has pore sizes of about 63 microns with approximately 37 percent of the area of the screen filter element being void space. The screen filter element 106 is made from threads which have a diameter of about 40 microns and is about 80 microns thick. The screen filter element 108 reoccurs as a second ply as screen filter element 110. The pore size of nylon screen filter element 108 is approximately 20 microns and about 16 percent of the area of screen filter element 108 is void space. Screen filter element 108 is made from threads which have a diameter of about 30 microns and is about 70 microns thick. Depth filter element 98 is a knitted polypropylene mesh having an uncompressed thickness of approximately 25 mils. The knit structure is prepared using a monofilament utilizing a knit and lay in type of knit structure. The structure has about 26 courses per inch and about 18 wales per inch. The structure has a weight of approximately 7 ounces per square yard. The knitted structure is formed on a 14 gauge machine using full threading and a closed stitch pattern of 1-0, 2-3 on the front bar and a lay in stitch pattern of 0-0, 4-4 on the back bar, using polypropylene monofilament having a thickness of 6 mils to give a structure which has a tendency to curl toward the closed stitch side into a cylindrical form.

The filter elements which remove the respective size fractions from blood during transfusion are indicated in FIG. 7 by the three stages. The largest size fraction is removed by stage I. Stage II removes the intermediate size fraction, and stage III removes the remaining fine size fraction of particulate debris. A screen element is not used in stage I because of the relative stability of the pore sizes in the knit structure. A screen is used as the last element in the second stage so as to provide a clean cut of the intermediate size fraction from the flowing blood. A double set of depth and screen filter elements is used in stage III as a safety measure to ensure that the desired removal of particulate matter has occurred. If elongated debris manages to slip through screen filter element 108, it is highly unlikely that after passing through depth filter 104 it will still be aligned axially so as to pass through screen filter element 110.

Referring particularly to FIG. 8, there is a further embodiment of a transfusion filter according to the present invention in which the reference numerals have the same meaning as assigned to them in FIG. 7. A double ply of depth filter 98 is employed both to provide structural stability to the filter cartridge, particularly during the manufacturing of the filter, and to provide a more complete elimination of the large size fraction before reaching the second stage.

The transfusion filter cartridge illustrated in FIG. 9 is similar to that shown in FIG. 7 except that a structural large pore screen element has been added to the outer circumference of the filter cartridge so as to ensure its structural integrity. As illustrated, the structural screen 112 has pore size openings of approximately 800 microns which is too large to perform any significant filtering function. The structural screen 112 is approximately 95 percent void area so that it does not substantially impede the flow of blood into the active filtering elements. The reference numerals in FIG. 9 have the same meanings assigned to them in FIGS. 7 and 8.

Referring particularly to FIG. 10, there is illustrated generally at 114 an exploded cross-sectional view taken along a radial flow path through a perfusion filter cartridge according to the present invention. The first stage is formed by filter element 98 which is a knitted structure having the characteristics described previously with reference to FIGS. 7 through 9. The second stage is provided by a depth filter element 116 and a screen filter element 106. The depth filter element 116 in the embodiment illustrated is a polyurethane felt having pore sizes which will generally retain particulate material which has particle sizes in excess of approximately 75 microns. Depth filter element 116 has an uncompressed thickness of about one-sixteenth inch and a weight of about 6 ounces per square yard. The depth filter element 116 has a pore count of approximately 90 pores per linear inch. The screen filter element 106 has the same characteristics previously described hereinabove with reference to element 106 in FIGS. 7 through 9. The third stage in perfusion filter cartridge 114 consists of two plies each of depth filter element 118 and screen filter element 108. Screen filter 108 has the characteristics previously described with reference to element 108 in FIGS. 7 through 9. Depth filter element 118 is a polyurethane felt which will generally retain particulate material which has particle sizes in excess of approximately 50 microns. The depth filter element 118 has an uncompressed thickness of about three thirty seconds of an inch and a weight of about 14 ounces per square yard. The depth filter element 118 has a specific area of about 1,385 square feet per square foot of felt. Depth filter 118 has a pore count of approximately 100 pores per linear inch. Perfusion filter cartridge 114 is intended for use in extracorporeal circulation circuits where there may be a large flow rate of as much as 6 to 8 or even 10 liters per minute and inlet pressures of as much as 250 millimeters of mercury or even more.

Referring particularly to FIG. 11, there is illustrated generally at 120 an exploded cross-sectional view of a cardiotomy filter cartridge. The cross-sectional view of cardiotomy filter cartridge 120 is taken along a radial flow path through that cartridge. Cardiotomy filter cartridge 120 includes three stages, the first of which is provided by knit structure 98. The second stage is provided by depth filter 116 and screen filter element 106. The third stage is provided by a double ply of depth filter element 118 and screen filter element 108. The various filter elements referred to by reference numeral 98, 106, 108, 116, and 118 have the characteristics described previously for like numbered elements in FIGS. 7 through 10. The cardiotomy filter cartridge 120 is intended for use in an extracorporeal circulation circuit where high flow rates and elevated pressures are encountered.

Referring particularly to FIG. 12, there is illustrated generally at 122 a cardiotomy reservoir filter cartridge. The cardiotomy filter cartridge 122 includes four stages, the first of which is a silicone coated defoamer filter element 124. The polyurethane defoamer 124 is a foam structure having a compressed thickness of about three-eighths of an inch, a density of about 1.75 pounds per cubic foot. The pore sizes in defoamer 124 are such that the minimum particle sizes retained on the filter element range from approximately 450 microns to 550 microns. The pore sizes are so large in defoamer 124 that very little of the particulate matter is filtered out by this element. The filter elements 98, 106, 108, 116, and 118, respectively, in cardiotomy reservoir filter cartridge 122 have the same characteristics as described in reference to the corresponding elements in FIGS. 10 and 11.

Referring particularly to FIG. 13, there is illustrated generally at 126 a transfusion filter cartridge in the unwound configuration. Transfusion filter cartridge 126 includes a depth filter band 128 and a screen filter band 130. A core 132 is provided to support the filter cartridge and receive blood therefrom. The screen filter band 130 includes two screen filter segments indicated at 108 and 106. Segments 108 and 106 are joined together at their abutting edges so as to form a single continuous band. The screen filter elements 106 and 108 have the characteristics described previously with regard to these reference numerals in FIGS. 7 through 12. Depth filter band 128 is constructed by edge welding the two abutting edges of depth filter elements 98 and 100. The joining of these two segments produces a continuous band. The filter elements 98 and 100 have the characteristics described previously with reference to these reference numerals in FIGS. 7 through 12. As shown, the two bands are placed in registry with one another so that the filter element 108 forms the innermost ply of the filter cartridge 126 as the bands are spirally wound around core 132 to form a cylindrical filter cartridge.

Referring particularly to FIG. 14, there is a further embodiment of a filter cartridge indicated generally at 134 in which there is a single composite band with an outer structural member which is not a part of the composite band. The several filter segments are joined together at a common joint 136 where there respective edges abut one another. The various filter elements identified by reference numerals 98, 100, 106, and 108 have the characteristics described previously for the elements to which these reference numerals are assigned in, for example, FIGS. 7 through 9. Structural element 138 is a knit structure which has a very large pore size and which serves to give the cartridge structural support during its final assembly, transportation, storage, and use.

Referring to FIG. 15, there is illustrated generally at 140 a plurality of bands prior to their being assembled into a filter cartridge. The various band segments indicated at 98, 100, 106, and 108 have the characteristics described previously with reference to elements to which the same reference numerals are assigned in, for example, FIGS. 7 through 12. Depth filter element 142 defines a segment which is constructed of a polyurethane foam having the capacity to retain large quantities of particulate material. Element 142 retains a size fraction in which the particle sizes are larger than approximately 35 microns. The segments which make up the depth filter band are joined at joint 144 and the segments which make up the screen filter band are joined at 146. The separate filter element 98 is separate from the other bands and is spirally wrapped to form the outer ply of the depth filter.

Referring particularly to FIG. 16, there is illustrated generally at 148 an integral filter cartridge band in which the various segments are all joined at their abutting edges to form one continuous band. The use of a continuous band facilitates the manufacture of the filter cartridge because only one continuous band structure need be handled in wrapping the filter cartridge. The various segments in the filter cartridge band 148 have the characteristics of the segments to which corresponding reference numerals are assigned elsewhere in these drawings.

Referring particularly to FIG. 17, there is illustrated generally at 150 a plan view of the filter cartridge bands which are illustrated in FIG. 13. The two segments in depth filter band 152 are joined at butt joint 154, and the two segments in screen filter band are joined at butt joint 158.

The approximate smallest particle sizes which are removed by the depth filter elements described herein are determined for the purposes of this invention by preparing an aqueous saline mixture including known quantities of various sizes of particulate material. The mixture is passed through the depth filter element and both the retained and passed fractions are analyzed.

The felt depth filters are conveniently prepared by irreversibly compressing a reticulated polyester or polyurethane open pore foam so that it has a final thickness of from about one-third to one-twelfth of the uncompressed thickness.

The foregoing specific embodiments as will be understood by those skilled in the art are illustrative only and modifications and changes may be made without departing from the spirit and scope of the accompanying claims. For example, the various filter elements may be filled or coated with various blood compatible organic or inorganic materials. Special surface treatments, such as mechanical, chemical, and electronic treatments may be applied to the surface of the fabrics, screens, and foams so as to alter their surface characteristics. One continuous band of woven fabric with a series of segments having different stitch patterns, yarn, denier, and fill counts may be used if desired. The blood filter cartridges may be incorporated within other devices such as disposable dialysis cartridges. In addition to joinder by adhesive, heat sealing, and the like a third element such as a blood compatible thread or staple device may be used to join the band segments together.

The physical dimensions of a blood filter cartridge according to the present invention are very small compared to the filtration capacity of the cartridge. For example, a transfusion blood filter of the type illustrated in, for example, FIGS. 1, 6, 7, and 13 may be constructed having a filter cartridge with an axial length of about 7 centimeters, a diameter of about 2½ centimeters with a core exterior diameter of about 1 centimeter and an interior core diameter of about 0.6 centimeter. The shell may conveniently have a maximum interior diameter of about 4 centimeters and a minimum interior diameter of about 3.4 centimeters. The tip of the conical distribution cap is conveniently spaced approximately 0.3 centimeter from the interior end of the inlet tube. The overall length of the blood filter from the tip of the inlet to the tip of the outlet may conveniently be about 13.5 centimeters.

What is claimed is:

1. A blood filter device having a normal blood flow direction therein comprising:
a filter means for filtering blood, said filter means including a plurality of porous screen and depth filter elements arranged in series with respect to normal blood flow direction through said filter means, said filter elements being positioned so that the pore sizes of said filter elements generally decrease in said normal blood flow direction, said filter means including at least three said filter elements which have different pore sizes to provide at least three filtration stages, the first filter element in at least the first two of said stages being a depth filter element, the first filter element in said filter means being a knit structure adapted to retain blood debris having a particle size in excess of approximately 100 microns and the last filter element in said filter means being a screen filter element having a pore size of approximately 20 microns.

2. A blood filter device of claim 1 wherein the first of said filtration stages includes at least two depth filter elements.

3. A blood filter device of claim 1 wherein said filter elements include at least two depth filter elements and at least two screen filter elements.

4. A blood filter of claim 1 wherein the filtration capacity of each of said stages is approximately equal.

5. Process for filtering blood comprising:
establishing a blood flow path through a series of porous filter elements from a first element to a last element;
subjecting blood flowing along said blood flow path to passage through generally decreasing pore sizes and generally decreasing filtering volumes, said pore sizes decreasing from a pore size adapted to retain blood debris having particle sizes of at least approximately 90 microns and larger to a pore size adapted to retain blood debris having particle sizes of approximately 20 microns and larger, there being at least three different pore sizes along said blood flow path;
permitting said blood to flow along and through said first element, said first element comprising a knitted fabric structure having a closed stitch pattern on one side and a lay in stitch pattern on one side and a lay in stitch pattern on the opposite side, said blood contacting said lay in stitch pattern first;
permitting said blood to flow through said last element, said last filter element comprising a screen filter element having a pore size of approximately 20 microns; and
at locations along said flow path intermediate said first and last elements, permitting said blood to flow through at least one depth filter and one screen filter.

6. Process of claim 5 including subjecting blood flowing along said blood flow path to passage through at least one screen filter element and at least one depth filter element.

7. A blood filter device for filtering undesired debris out of blood, said debris having particle sizes ranging from at least approximately 90 microns to approximately 20 microns, said debris being classifiable into a plurality of size fractions ranging from coarse to fine, and each said size fraction containing an approximate predetermined volume of debris for a given volume of blood, said blood filter device comprising:
a filter means for filtering blood including a plurality of porous filter elements, said filter elements being arranged in successive layers in a cylindrical form around a perforate axial core member to define a plurality of filtration stages from a first stage beginning at the outer periphery of said filter means to a last stage adjacent said core member, each of said stages having a filtration capacity, there being at least three such stages with a stage being provided for each said size fraction, whereby successively finer size fractions are retained in the respective stages as the blood flows from the first through the last of said stages, the first said filter element in the first said stage being a knitted mesh depth filter and the last stage being a knitted mesh depth filter and the last filter element in said filter means being a screen filter element having a pore size of approximately 20 microns, the filtration capacity for said given volume of blood of each of the said stages being at least approximately equal to the volume of debris in the size fraction to be retained therein.

8. A blood filter device of claim 7 wherein the filtration capacity for said given volume of blood of at least the first and second said stages is approximately equal to the volume of debris in the respective size fractions to be retained therein.

9. A blood filter device of claim 7 wherein at least the first filter element in each of the first two said stages is a depth filter element.

10. A blood filter device of claim 7 wherein the first filter element in said filter means is a depth filter element having a pore size sufficient to retain a size fraction which includes particle size in excess of approximately 100 microns.

11. A blood filter device of claim 7 wherein said filter means is in the form of a band and the said filter elements comprise segments of said band, said band being wrapped spirally into a cylinder.

12. A blood filter of claim 7 having three said filtration stages wherein the first said stage comprises a depth filter element, the second said stage comprises a depth filter element and a screen filter element, and the third said stage comprises a depth filter element and a screen filter element.

13. A blood filter device for filtering undesired, debris out of blood, said debris having particle sizes ranging from at least approximately 90 microns to approximately 20 microns, said debris being classifiable into a plurality of size fractions ranging from coarse to fine, and each said size fraction containing an approximate predetermined volume of debris for a given volume of blood, said blood filter device comprising:

a filter means for filtering blood including a plurality of porous filter elements spirally wrapped into a cylinder, said filter elements being arranged to define a plurality of filtration stages from a first stage to a last stage, said first stage being at the outer circumference of said cylinder, said cylinder normally in use being oriented vertically whereby blood flows from above said cylinder along the outer circumference of said cylinder and radially inwardly from said first to said last stage, there being at least three such stages with a stage being provided for each said size fraction, whereby successively finer size fractions are retained in the respective stages as the blood flows from the first through the last of said stages, the first said filter element in the first said stage being a depth filter and the last said stage including at least a screen filter element, said first filter element being a knitted structure having a closed stitch pattern on a first side and a lay in stitch pattern on a second side, said second side being at the outer circumference of said cylinder.

14. A blood filter device of claim 13 wherein the said filter means includes medications which are dispensed into the blood as it passes through the blood filter device.

15. A blood filter device of claim 13 wherein the said cylinder is closed at one end with a generally conical cap, said blood filter device being adapted to be normally positioned so that blood flows down over said conical cap and along said second side before passing through said plurality of filtration stages.

16. A blood filter device comprising:
a filter case having a generally annular cavity therein, a blood inlet and a blood outlet in said filter case, and an elongated, rigid, perforate core, said core, inlet and outlet being generally axially aligned along the longitudinal axis of said annular cavity, said blood filter device normally being oriented in use with said longitudinal axis generally vertical;

a generally cylindrical filter cartridge including a plurality of porous filter elements, said filter elements being arranged in successive layers in a cylindrical form around said core within said annular cavity, the pore sizes of said filter elements generally decreasing from the outer periphery of said filter cartridge toward said core, the radially outermost filter element in said filter cartridge being a knit monofilament fabric structure having a lay in stitch pattern on the radially outermost side thereof and a closed stitch pattern on the radially inner side thereof, said knit structure having a pore size sufficient to retain blood debris having particle sizes in excess of approximately 90 microns, the radially innermost filter element in said filter cartridge being a final screen filter element having a pore size of approximately 20 microns, said filter cartridge including in addition to said knit fabric structure and said final screen filter element at least one intermediate depth filter element and one intermediate screen filter element, the outer circumference of said filter cartridge being spaced radially from an inner wall of said annular cavity to define an annular therebetween, a generally conical cap closing the normally upper end of said generally cylindrical filter cartridge, the apex of said generally conical cap being adjacent said blood inlet, whereby blood flowing through said blood inlet flows over said apex, is distributed over the conical surface of said cap, flows over the periphery of said cap, flows down along said outer periphery, radially inwardly through said filter cartridge to said core, and out through said blood outlet.

17. A blood filter device comprising:
a plurality of filter elements arranged in a generally cylindrical form to define a plurality of filtration stages from a first stage at the outer circumference thereof to a last stage, the first said filter element in said first stage being a knit fabric structure having a closed stitch pattern on a first side and a lay in stitch pattern on a second side, said filter elements being positioned so that blood entering said filter contacts said second side first and flows along said second side and into said second side, whereby said knit fabric structure tends to curl toward said first side and blood flowing along said second side tends to form into a sheet.

* * * * *